United States Patent [19]

Kotani et al.

[11] Patent Number: 4,805,633
[45] Date of Patent: Feb. 21, 1989

[54] DISPLACEMENT SENSOR

[75] Inventors: Tsutomu Kotani, Kamagaya; Minoru Takahashi, Funabashi, both of Japan

[73] Assignee: TDK Corporation, Tokyo, Japan

[21] Appl. No.: 140,043

[22] Filed: Dec. 31, 1987

[30] Foreign Application Priority Data

Jan. 26, 1987 [JP] Japan .................................. 9635/87

[51] Int. Cl.$^4$ ................................................ A61R 7/04
[52] U.S. Cl. ........................................ 128/715; 381/67
[58] Field of Search ................ 324/247; 128/715, 773, 128/687; 381/67, 177

[56] References Cited

U.S. PATENT DOCUMENTS

| | | | |
|---|---|---|---|
| 2,294,015 | 8/1942 | Salb et al. ............................ | 128/715 |
| 3,555,187 | 1/1971 | Rowley ................................ | 128/715 |
| 4,458,687 | 7/1984 | Dickson .............................. | 128/715 |
| 4,765,321 | 8/1988 | Mohri ................................. | 128/715 |

*Primary Examiner*—A. Michael Chambers
*Attorney, Agent, or Firm*—Burgess, Ryan & Wayne

[57] ABSTRACT

A displacement sensor or an electrocardiogram attaches a permanent magnet chip directly on a living body, and movement or vibration of the living body is sensed by measuring flux by said magnet. The displacement sensor has a magnet assembly having an adhesive film mounting a permanent magnet at the center of the film supported on a bottom ring which has a plurality of upright walls with jaws, for detachably engaging the magnet assembly with a sensor body. The sensor body has saturable inductors which are placed in flux by said magnet and are coupled with a process circuit having an astable multivibrator with a collector load by said saturable inductors and a low-pass filter connected to the output of the multivibrator. The magnet assembly is first adhered on a living body, then, the sensor body is engaged with the same by engaging said jaws with a ring on the sensor body, then, the process circuit provides an output signal reflecting the movement of a living body.

6 Claims, 5 Drawing Sheets

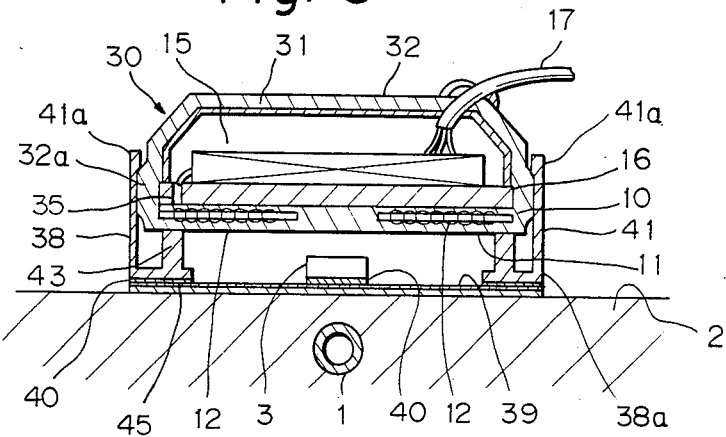
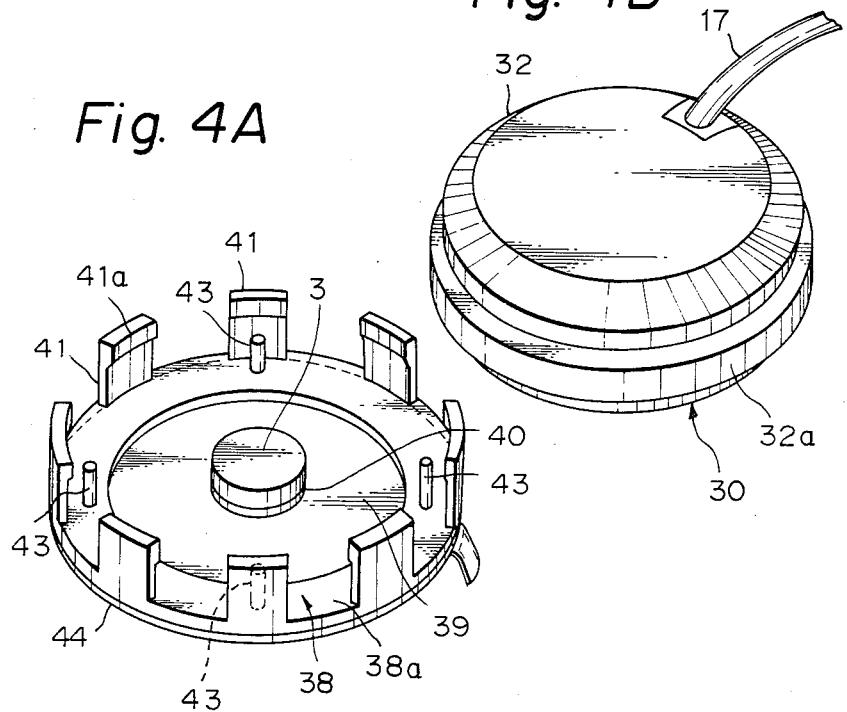

DISPLACEMENT SENSOR

BACKGROUND OF THE INVENTION

The present invention relates to a displacement sensor, in particular, relates to such a device which senses the displacement or vibration of a living body. The present invention is applicable to a stethoscope for medical and mechanocardiogram purposes.

Conventionally, an acoustic stethoscope has been used for diagnosing the internal conditions of a living body. A prior stethoscope places a diaphragm on a surface of a living body, and the vibration of the diaphragm is listened to by a doctor through a stethoscope tube.

Therefore, a prior stethoscope has the disadvantage that only a single doctor can listen to the sound of the vibration of the heart valves of a living body, but it cannot be listened to by a plurality of persons. Further, a prior stethoscope has the disadvantage that a doctor cannot listen to the sound of a heart beat with a frequency less than 20 Hz, and the output of the stethoscope can not be recorded.

On the other hand, a prior electrocardiogram records pulsation or drive electrical signal of a heart, but it does not record the actual mechanical movement of a heart. Therefore, if there is something wrong with a heart, such as valve disease and arteriosclerosis, it could not be detected by a prior electrocardiogram. Conventional mechanocardiograph sensors for detection of heart movement have disadvantage due to their difficulty of usage.

The present applicant proposed an improved displacement sensor as shown in FIG. 1, which solves the above problem, in U.S. patent application Ser. No. 931,699 now U.S. Pat. No. 4,765,321, issued 08/23/88 and EP Patent application No. 86308971.0. The displacement sensor of FIG. 1 uses the principle of inductance control by a movable permanent magnet.

In the figure, the displacement sensor or the stethoscope 101 has a main body 102, a diaphragm 103 and a sensor 110.

A hollow rigid tube 108 is coupled with the main body 102, and a flexible tube 104 is coupled with said hollow rigid tube 108. Accordingly, an acoustic vibration in empty space 105 in the main body 102 propagates through the rigid tube 108 to the flexible tube 104, far end of which is to be inserted into the ear of a doctor. The main body 102 has a screw 109 at the outer surface of the same, and the diaphragm 103 is engaged with that screw. The sensor 110 is mounted between the diaphragm 103 and the main body 102.

The sensor 110 functions to generate an electrical signal according to the vibration of the diaphragm 103, and said sensor 110 has a magnetic pole M (a small permanent magnet), a group of inductors 112 which cause inductance variation according to displacement of said magnetic pole M, and a holder 111 for fixing the inductors 112. The sensor terminal 105a is mounted on the main body 102 so that the lead wires of said inductors 112 are coupled with the sensor cable 107 through the sensor terminal 105a. The far end of the sensor cable 107 is coupled with a processor 106 which processes the signal from the sensor 110.

Accordingly, the stethoscope of FIG. 1 functions both for a prior stethoscope which propagates acoustic vibration to an ear, and for an electric stethoscope which provides electrical output information according to the vibration of the diaphram 103.

However, we realized some problems of the stethoscope of FIG. 1. First, some noise is induced on a cable 107, because the processor circuit 106 is separated from the stethoscope 101. Furthermore, we realized that it does not need to double as an acoustic stethoscope. More importantly, to put the stethoscope accurately on an affected part of a living body for a long time is difficult. Also, since the stethoscope of FIG. 1 is applied on an affected part with a doctor's hand, the electrical output depends upon the pressure put by the stethoscope on an affected part.

In order to solve the above problems, we made a first step a displacement sensor as shown in FIG. 2, which uses the same electrical principle as that of FIG. 1, but a processor circuit is included in a stethoscope head, an acoustic stethoscope is removed, and a stethoscope is adhered to an affected part of a living body instead of applying the same by hand.

In FIG. 2, a permanent magnet 3 is put on an affected part 2 of a living body 1 by an adhesive thin film 4. The sensor body 6 has a recess 8 at the bottom of the housing 7. The sensor body 6 is put on the affected part so that the permanent magnet 3 is within the recess 8. The non-magnetic conductive shield case 9 is inserted in the housing 7, and an even number of inductors 12 each having a magnetic wire 10 and a coil 11 wound on the wire 10 are arranged radially with an equal angular interval. The inductors are molded on the inductor shelf 4 by plastics 13. The printed circuit board 16 which mounts a processor circuit 15 is positioned on the inductor shelf 14 with some spacing. A lead wire connects the process circuit 15 with an external circuit.

However, we found in the experiment that the structure of FIG. 2 has the disadvantage that it is difficult to locate the sensor body 6 so that the center of the recess 8 coincides with the center of the permanent magnet 3. It should be noted that the diameter of the magnet is about 4 mm, and the inner diameter of the recess 8 is about 10 mm so that the magnet 4 can vibrate freely in vertical direction. The locational error of the sensor body 6 causes the error of an output signal of the displacement sensor, and/or deteriorates the essential sensitivity of the sensor.

SUMMARY OF THE INVENTION

It is an object, therefore, of the present invention to overcome the disadvantages and limitations of a prior stethoscope and/or a prior displacement sensor by providing a new and improved displacement sensor which is used as a stethoscope.

It is also an object of the present invention to provide a displacement sensor which includes a processor circuit, and is free from the positioning error of a permanent magnet.

It is also an object of the present invention to provide a displacement sensor which is put on an affected part of a living body without pushing the same with a hand.

The above and other objects are attained by a displacement sensor having; a sensor body having a substrate (16), a plurality of saturable inductors connected alternately in series mounted on one surface of said substrate radially with a predetermined angular period, each of said saturable inductors having a saturable magnetic core and a coil wound on the core, a process circuit (15) for processing output of said saturable inductors mounted on the other surface of said substrate, a lead wire coupled with said process circuit for supplying power to said process circuit and obtaining output of the process circuit, a shield case (31) surrounding said process circuit, and a housing (32) for securing above members having a ring (32a) on external wall of the housing; and a magnet assembly having a bottom ring (38a) with a plurality of upright wall chips (41) positioned perpendicularly at periphery of said bottom ring, a film (39) having a permanent magnet at center of said film attached to said bottom ring, each of said wall chips having a jaw at the extreme end so that said jaw engages detachably with said ring (32a) of the housing (32), and plurality of bars (43) fixed to said bottom ring (38) so that it touches with said sensor body when it is engaged with the magnet assembly, and said magnet is positioned close to said saturable inductors.

BRIEF DESCRIPTION OF THE DRAWINGS

The foregoing and other objects, features, and attendant advantages of the present invention will be appreciated as the same become better understood by means of the following description and accompanying drawings wherein;

FIG. 3 shows a cross section of a displacement sensor according to the present invention, FIGS. 4A and 4B show perspective view of the displacement sensor according to the present invention.

DESCRIPTION OF THE PREFERRED EMBODIMENTS

Figure 5:
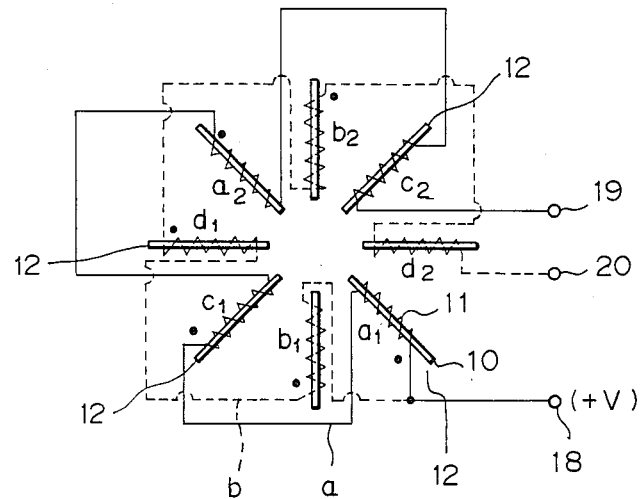
FIG. 5 shows arrangement of the coils of the displacement sensor according to the present invention.
Figure 6:
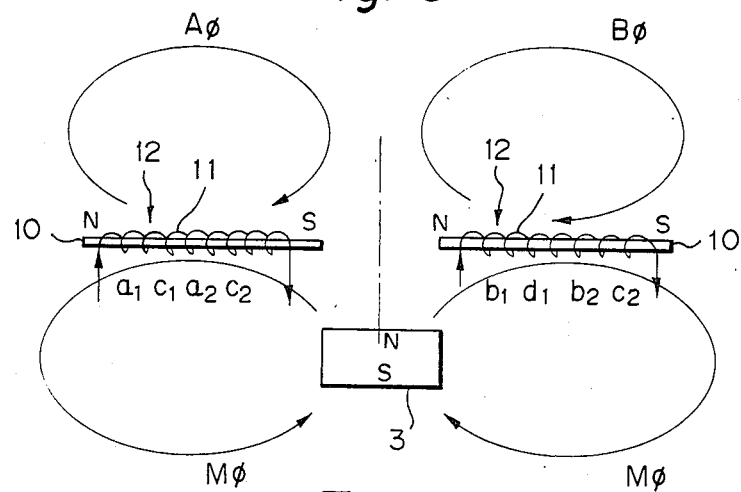
FIG. 6 shows the operation of the inductors according to the present invention.

The displacement sensor according to the present invention is now described in accordance with FIGS. 3, 4A and 4B. In those figures, the numeral 16 is a substrate. On one surface of the substrate 16 which faces with a permanent magnet 3, an even number of inductors 12 each having a saturable magnetic wire 11 made of amorphous material and a coil 11 wound on the wire 10 are located radially as shown in FIG. 5. The inductors 12 are positioned radially with a predetermined angular interval as shown in FIG. 5. On the other side of the substrate 16, the process circuit 15 which processes an output signal of the inductors 12 is mounted. The process circuit 15 is shielded by a non-magnetic conductive case 31 made of bronze or aluminum. The lead wire 17 is connected to the process circuit 15 for an external connection. The housing 32 is obtained by molding the inductors 12, the substrate 16 and the shield case 31 by using dielectric plastics. Thus, the sensor body 30, which has the above structure, is obtained. It should be noted that the inductors 12 and the shield case 31 are fixed on the substrate 16 by using adhesive, when the molding process is carried out for preventing positional error of the members.

The numeral 38 is a circular frame made of plastics, which mounts the permanent magnet 3, and is detachably engaged with the sensor body 30. The frame 38 has a ring shaped bottom ring 38a, a circular flexible non-magnetic adhesive film 39 which is adhered to the bottom ring 38a through the plastics adhesive 40. The permanent magnet chip 3 is fixed at the center of the film 39 through the plastics adhesive 40. The film 39 is preferably thin so that it does not disturb the movement of a living body, and is transparent. A non-woven cloth which has uniform expansion property in all the directions is preferably used as said film 39.

The frame 38 has a plurality of upright walls 41, each of which has a projected jaw 41a at the end of the wall 41 so that the jaw 41a engages detachably with the ring 32a which is projected on the outer surface of the housing 32 as shown in FIG. 3. Preferably, more than four walls 41 are provided. The bottom ring 38a has a plurality of bars 43 with a predetermined angular distance so that said bar 43 functions as a stopper to position the frame 38 when the frame 38 is engaged with the housing 32. The numeral 44 is a non-adhesive cover which is attached on the surface of said adhesive film 39.

In operation, it should be noted that the magnet assembly of FIG. 4A is, first, separated from the sensor body of FIG. 4B.

The cover 44 is removed, so that the adhesive 45 on the film 39 appears, then, the magnet assembly is adhered on a skin 2 of a living body so that the permanent magnet 3 locates on an affected part. When the film 39 is transparent, the magnet is accurately positioned on an affected part. Next, the sensor body 30 is engaged with the frame assembly.

It should be appreciated that when the magnet assembly is engaged with the sensor body 30, the magnet 3 is positioned at the center of the inductors group 12, since the rear surface of the housing 32 contacts with the top of the bars 43, and the frame 38 is resiliently engaged with the ring 32a by the resilient property of the material of the walls 41.

It should be appreciated that the sensor body 30 is engaged with and/or detached from the magnet assembly with weak strength, since the walls 41 are separated into a plurality of chips.

The electrical operation of the present displacement sensor is similar to that of the U.S. patent application Ser. No. 931,699 now U.S. Pat. No. 4,765,321, issued 8/23/88 (EP application No. 86308971.0), and U.S. patent application No. 881,110 now U.S. Pat. No. 4,739,323, issued 04/19/88.

The inductors 12 are saturable inductors having an amorphous core, and the inductors 12 are positioned radially as shown in FIG. 5. The inductors 12 are connected alternately in series as shown in FIG. 5, so that the inductors $a_1$, $c_1$, $a_2$, and $c_2$ are connected in series, and the inductors $b_1$, $d_1$, $b_2$ and $d_2$ are connected in series. Only a pair of inductors (for instance, $a_1$ and $a_2$, would be enough for merely sensing the magnetic field, but the radially positioned arrangement and the alternate series connection as shown in FIG. 5 allow to get rid of the influence of the earth's magnetism.

The amorphous wire 10 of the inductors is for instance has the composition $Co_{68}Fe_4Si_{13}B_{15}$ in atomic percent, and the diameter is 110 μm, and the length is 3 mm, in one embodiment.

It should be noted that the total inductance of the first serially connected inductors ($a_1$, $c_1$, $a_2$, $c_2$) differs from that of the second serially connected inductors ($b_1$, $d_1$, $b_2$, $d_2$) which are shown by dotted line, depending upon the position of the permanent magnet 3. FIG. 5 shows that situation.

In FIG. 5 where the magnet 3 has the north pole N close to the inductors 12, the magnetic flux $M_\phi$ by the magnet 3 is cancelled by the flux $B_\phi$ by the current in the coil 11 as shown in right half of FIG. 5. On the other hand, the flux $M_\phi$ by the magnet 3 is added to the flux $A_\phi$ by the current in the coil 11. When the flux by the magnet is in the same direction as that of the current, the magnetic core 10 would be saturated.

Thus, the inductance of the first serially connected inductors differs from that of the second serially connected inductors. And, the difference of the inductance between two serially connected inductors depends upon the position of the permanent magnet 3. Thus, the position or the vibration of the permanent magnet is sensed by measuring the inductance difference.

Figure 7:
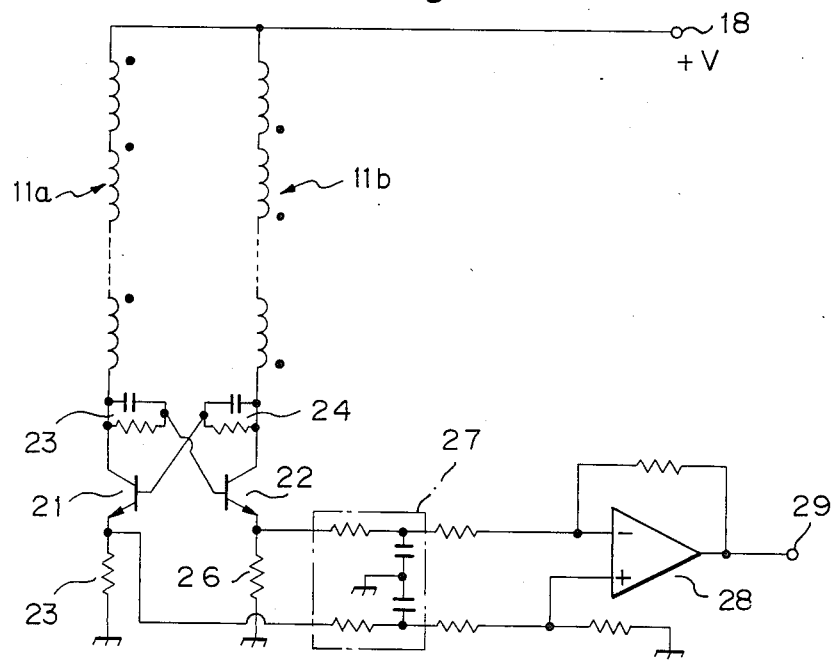
FIG. 7 shows the process circuit of the displacement sensor according to the present invention.

The inductance difference is measured by the process circuit. FIG. 7 is the embodiment of the process circuit, which is essentially an astable multivibrator.

One end of the first serially connected coils 11a and the second serially connected coils 11b is commonly coupled with the power source 18 (+V), and the other ends of those coils are connected to the collectors of the transistors 21, and 22, respectively. The emitters of those transistors are grounded through the resistors 23 and 26, respectively. The parallel circuits 23 and 24 each having a resistor and a capacitor connect the base and the collector of the transistors. The emitters of the transistors are connected to the low-pass filter 27 (integration circuit), output of which is coupled with the DC amplifier 28, which provides the displacement output 29.

It should be noted that the oscillation period of an astable multivibrator depends upon the inductance connected to the collector. Since that inductance depends upon the location of the magnet, the half period of the oscillation of the astable multivibrator depends upon the location of the magnet. The low-pass filter 27 attenuates the AC component of the astable multivibrator, and provides only the DC component, which reflects the location of the permanent magnet.

Figure 8:
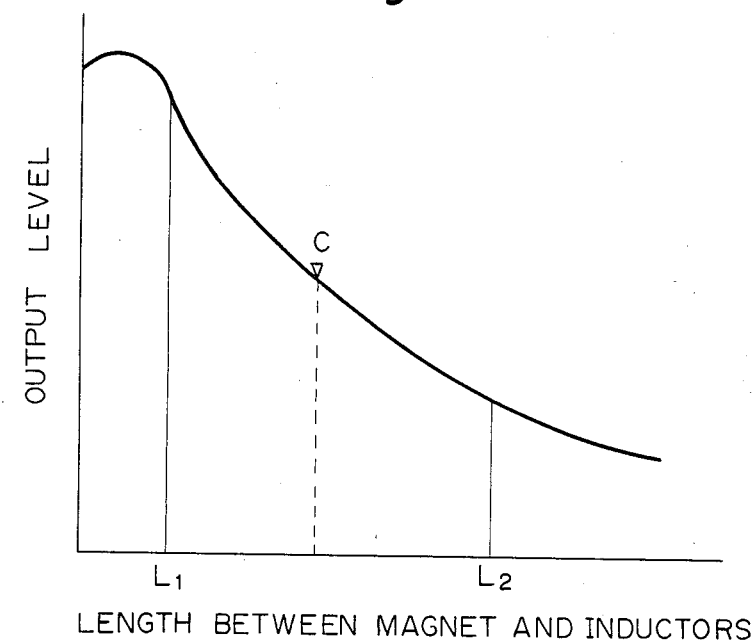
FIG. 8 and FIG. 9 show operational curves of the displacement sensor according to the present invention.

FIG. 8 shows the curve between the location of the magnet (horizontal axis), and the output voltage at the terminal 29. It should be noted that the curve has the essentially linear portion when the location of the magnet is between $L_1$ and $L_2$. Therefore, the system is designed so that the magnet is positioned at the center C of the linear portion. The oscillation frequency of the astable multivibrator is, preferably, in the range between 100 kHz and 500 kHz. The time constant of the displacement sensor, or the quickness of the response of the sensor depends upon the time constant of the low-pass filter 27. Therefore, that low-pass filter is designed according to the velocity of the movement of the object to be sensed.

Figure 1:
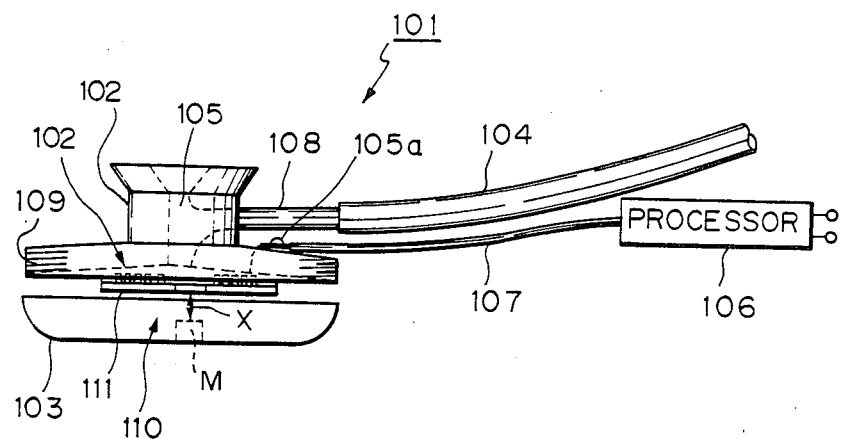
FIG. 1 shows a structure of a prior displacement sensor.
Figure 2:
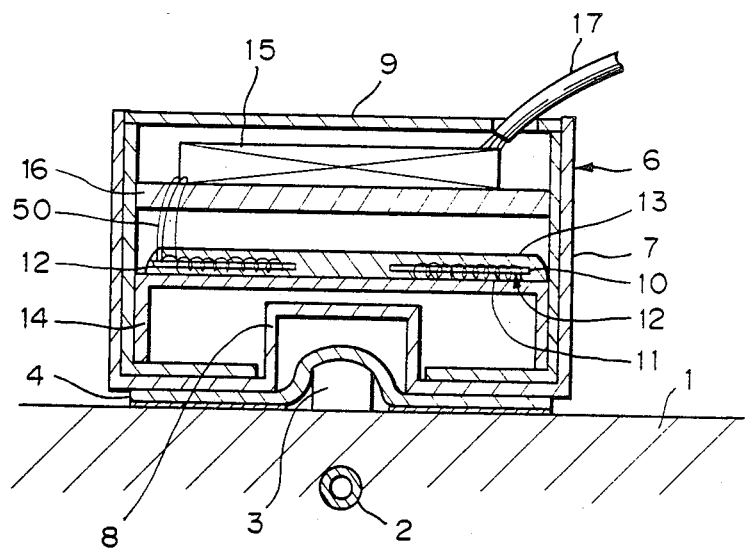
FIG. 2 shows another structure of a prior displacement sensor.
Figure 9:
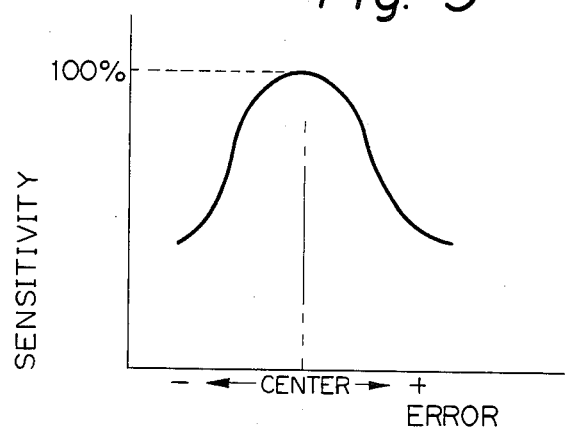

FIG. 9 shows the curve between the sensitivity (vertical axis) and the locational error of the permanent magnet (horizontal axis). The sensitivity is of course the maximum when the error is zero, or the magnet is positioned at the center of the inductors. When the magnet has the positional error, the sensitivity decreases as shown in FIG. 9. It should be appreciated that the positional error of the magnet according to the present invention is very small, as compared with that of a prior art of FIG. 1 or FIG. 2, since the magnet is attached on the center of the magnet assembly, which is coupled detachably with the sensor body by using a snap action of upright walls.

Thus, the movement of an affected portion of a living body is sensed by the movement of the permanent magnet, and the movement of the permanent magnet is sensed by the inductance difference, which is measured by the process circuit. Thus, the process circuit provides the output signal depending upon the movement of a living body.

Some modifications are of course possible to those skilled in the art. For instance, a wall 41 with a jaw 41a may be mounted to a sensor body, instead of a magnet assembly.

From the foregoing, it will now be apparent that a new and improved displacement sensor has been found. It should be understood of course that the embodiments disclosed are merely illustrative and are not intended to limit the scope of the invention. Reference should be made to the appended claims, therefore, rather than the specification as indicating the scope of the invention.

What is claimed is:

1. A displacement sensor comprising;
    a sensor body having a substrate (16), a plurality of saturable inductors connected alternately in series mounted on one surface of said substrate radially with a predetermined angular period, each of said saturable inductors having a saturable magnetic core and a coil wound on the core, a process circuit (15) for processing output of said saturable inductors mounted on the other surface of said substrate, a lead wire coupled with said process circuit for supplying power to said process circuit and obtaining output of the process circuit, a shield case (31) surrounding said process circuit, and a housing (32) for securing above members having a ring (32a) on external wall of the housing, and
    a magnet assembly having a bottom ring (38a) with a plurality of upright wall chips (41) positioned perpendicularly at periphery of said bottom ring, a film (39) having a permanent magnet at center of said film attached to said bottom ring, each of said wall chips having a jaw at the extreme end so that said jaw engages detachably with said ring (32a) of the housing (32), and a plurality of bars (43) fixed to said bottom ring (38) so that it touches with said sensor body when it is engaged with the magnet assembly, and said magnet is positioned close to said saturable inductors.

2. A displacement sensor according to claim 1, wherein said film is transparent.

3. A displacement sensor according to claim 1, wherein said film is adhesive, and is adhered on a body which is subject to sense.

4. A displacement sensor according to claim 1, wherein more than four wall chips are provided.

5. A displacement sensor according to claim 1, wherein said saturable magnetic core is made of amorphous material.

6. A displacement sensor according to claim 1, wherein said process circuit has an astable multivibrator with a collector load by said saturable inductors, and a low-pass filter coupled with output of said multivibrator to obtain displacement output signal according to position of said magnet.

* * * * *